United States Patent [19]

Hamminga et al.

[11] Patent Number: 5,198,437
[45] Date of Patent: Mar. 30, 1993

[54] 1,7-ANNELATED INDOLECARBOXYLIC ACID ESTERS AND AMIDES

[75] Inventors: Derk Hamminga; Hans H. Haeck; Ineke Van Wijngaarden; Wouter Wouters, all of Weesp, Netherlands

[73] Assignee: Duphar International Research B.V., Weesp, Netherlands

[21] Appl. No.: 628,109

[22] Filed: Dec. 17, 1990

Related U.S. Application Data

[63] Continuation-in-part of Ser. No. 280,886, Dec. 7, 1988, Pat. No. 4,985,420.

Foreign Application Priority Data

[30]
Dec. 10, 1987 [NL] Netherlands ............... 8702981

[51] Int. Cl.$^5$ ............... C07D 519/00; A61K 31/54; A61K 31/535; A61K 31/495
[52] U.S. Cl. ............... 514/224.5; 544/14; 544/32
[58] Field of Search ............... 544/32, 14; 514/224.5

[56] References Cited

U.S. PATENT DOCUMENTS

| | | | |
|---|---|---|---|
| 4,910,193 | 3/1990 | Buchheit | 514/216 |
| 4,985,420 | 1/1991 | Hamminga | 540/472 |

OTHER PUBLICATIONS

Van Wijngaarden, Chem Abs 114, 164228d (1990).
Journal of Heterocyclic Chemistry, vol. XI, Jun. 1974, pp. 387-393.

Primary Examiner—Mark L. Berch
Attorney, Agent, or Firm—Stevens, Davis, Miller & Mosher

[57] ABSTRACT

1,7-Annelated esters and amides of indolecarboxylic acids having formula 2,

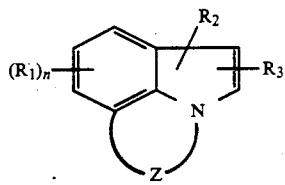

wherein
$R_1$ is halogen;
n has a value of 0–2;
Z together with the carbon atom, the nitrogen atom and the intermediate carbon atom, forms a heterocyclic group consisting of 6 ring atoms in which, besides the nitrogen atom already present, a second hetero atom of S is present, which ring may be annelated with a benzene ring;
$R_3$ is hydrogen, halogen, alkyl, alkoxy or alkylthio having 1–4 carbon atoms; and
$R_2$ is a group —CO—Y—$R_7$ wherein Y is an oxygen atom, or a group —$NR_6$, wherein $R_6$ is hydrogen or alkyl having 1–3 C-atoms, and $R_7$ represents a group of the formula

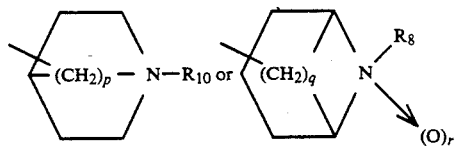

wherein p has the value 1 or 2, q has the value 2 or 3, $R_8$ is hydrogen or alkyl or hydroxyalkyl having 1 or 2 C-atoms, r is 0 or 1, and $R_{10}$ is absent. The compounds and their salts are very strong selective antagonists of neuronal 5-hydroxytryptamine (5-HT) receptors, and can be used for the treatment of symptoms which are caused by over-stimulation of those receptors.

6 Claims, No Drawings

1,7-ANNELATED INDOLECARBOXYLIC ACID ESTERS AND AMIDES

This application is a continuation-in-part of our prior application Ser. No. 280,886, filed Dec. 7, 1988 U.S. Pat. No. 4,985,420.

The invention relates to new 1,7-annelated indolecarboxylic acid esters and -amides of cyclic and polycyclic alcohols or amines, in which cyclic or polycyclic ring a carbon atom has been replaced by a secundary or tertiary nitrogen atom or the N-oxide thereof.

It is known inter alia from European Patent Application 85810595.0 (publication no. 0.189.002) that compounds of the general formula 1

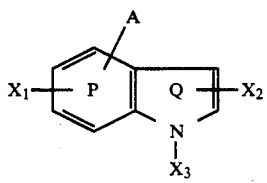
(1)

wherein $X_1$ and $X_2$ are hydrogen, halogen, alkyl, alkoxy, hydroxy, amino, alkylamino, dialkylamino, mercapto or alkylthio, $X_3$ is hydrogen, alkyl, alkenyl, aryl or aralkyl, and A is a group —B'—C'—D' which is bound to ring P or ring Q, wherein B' is the group —CO or —SO$_2$, C' is the group —O— or —NH— and D' is a heterocyclic, nitrogen-containing group, are 5-HT$_3$ antagonists which may be used for the treatment of gastrointestinal syndromes induced by serotonin.

It has now been found that the new compounds of formula 2

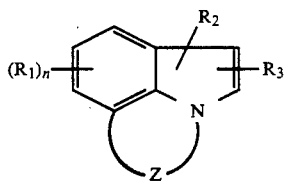
(2)

wherein
$R_1$ is straight or branched alkyl having 1-4 C-atoms; fluorinated or hydroxylated alkyl having 1-4 C-atoms, or $R_1$ is straight or branched alkenyl or alkynyl having 2-4 C-atoms, or $R_1$ is straight or branched alkoxy or alkylthio having 1-6 C-atoms which may be substituted with one or more fluorine atoms or hydroxyl groups, or with one optionally substituted phenyl group, or two alkoxy groups $R_1$ bound to adjacent carbon atoms may form a ring consisting of 5-7 ring atoms, or $R_1$ is straight or branched $(C_{1-4})$alkoxy-, $(C_{1-4})$alkylthio- or alkyl-$(C_{1-4})$sulphonyl-$(C_{1-2})$alkyl which may comprise one or more fluorine atoms or hydroxyl groups, or $R_1$ is an alkoxycarbonyl methyl group having 1-6 C-atoms in the alkoxy group, or $R_1$ is a group $R_4R_5N$—CO—CH$_2$—, $R_4R_5N$—CO— or $R_4R_5N$—SO$_2$— wherein $R_4$ and $R_5$ independently of each other are hydrogen, alkyl having 1-3 C-atoms, or together with the nitrogen atom form a heterocyclic 5- or 6-ring, or $R_1$ is hydroxy, halogen, cyano straight or branched alkoxycarbonyl having 1-6 C-atoms in the alkoxy group; n has the value 0-3;

Z together with the carbon atom and the nitrogen atom and the intermediate carbon atom forms a heterocyclic group consisting of 5-8 ring atoms, in which, besides the nitrogen atom already present, a second hetero atom from the group N, O, S, S-O, SO$_2$ or C=O may be present, which ring may be substituted with 1-3 alkyl groups having 1-4 C-atoms, a phenyl group or a spiroalkyl group $(C_{2-5})$, or which ring may be annelated with a saturated or non-saturated carbocyclic or heterocyclic ring consisting of 5- or 6-ring atoms which may be substituted with halogen or alkyl having 1-4 C-atoms;

$R_3$ is hydrogen, halogen, alkyl, alkoxy or alkylthio having 1-4 C-atoms, and $R_2$ is the group —B—C—D, wherein B is the group —CO—, C is oxygen or $NR_6$, wherein $R_6$ is hydrogen, $(C_{1-7})$ alkyl or benzyl, and D is a group $(CH_2)_m$-$R_7$, wherein m has the value 0, 1 or 2 and $R_7$ is a carbocyclic ring system in which one carbon atom has been replaced by a secondary or tertiary nitrogen atom or the N-oxide thereof;

and the pharmacologically acceptable acid addition salts thereof are very strong and selective antagonists of "neuronal" 5-hydroxytryptamine (5-HT) receptors.

The group D is preferably a group of the formula

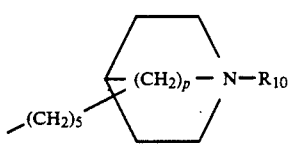
(3)

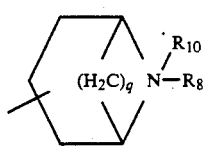
(4)

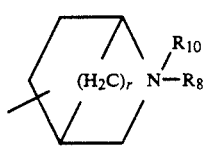
(5)

wherein p has the value 1 or 2, s has the value 0, 1 or 2, q is 2, 3 or 4, r is 1, 2 or 3, and wherein $R_8$ is hydrogen, $(C_{1-7})$alkyl, $(C_{3-8})$cycloalkyl, $(C_{3-8})$cycloalkyl-$(C_{1-2})$-alkyl, $(C_{3-5})$alkenyl, $(C_{3-5})$alkynyl, or wherein $R_8$ is a group $(CH_2)_t$-$R_9$, wherein t is 1 or 2 and $R_9$ is hydroxy, or $R_9$ is the phenyl group, thienyl group, pyrrolyl group or furyl group, which groups may be substituted with 1 or 2 substituents, and $R_{10}$ is absent or is an oxygen atom.

Suitable acids with which the compounds of formula 1 according to the invention can form pharmaceutically acceptable acid addition salts are hydrochloric acid, sulphuric, phosphoric acid, nitric acid, and organic acids, for example, citric acid, fumaric acid, maleic acid, tartaric acid, acetic acid, benzoic acid, p-toluene-sulphonic acid, methane sulphonic acid and the like.

Both the racemates and (geometric) isomers and the individual enantiomers of compounds of formula 2 belong to the invention.

The antagonistic activity of the compounds of formula 2 on the respons induced by 5-HT or by 2-methyl-5-HT was determined and measured in the Bezold-Jarisch reflex test in rats. The affinity for "neuronal"

5-HT receptors was determined and measured by means of the displacement of ($^3$H) GR 38032 F of neuroblastoma cells.

On the basis of the antagonistic activity of this type of 5-HT receptors, the compounds may be used for the treatment of symptoms which are caused by over-stimulation of these receptors a) in the gastrointestinal system (nausea and vomitting as a result of exogenic factors, for example, cancer therapy, or endogenic factors, for examples, stasis of the stomach and migraine) ulcer, dyspepsia, spasms, irritable bowel syndrome, etc., or b) in the central nervous system (hallucinations, delusions, manias, anxiety, pain, improvement of vigilance etc.), or c) in the cardiovascular system, for example, spasms of the vessels, arrhytmia, etc, or d) for the relief or prevention of withdrawal syndromes induced for instance by abuse of drugs, or e) in the respiratory system (including nasal disorders or disorders of the bronchi and lungs).

The compounds according to the invention and their salts can be brought into a form suitable for administration, for examples, pills, tablets, coated tablets, capsules, powder, injection liquids and the like by means of techniques conventionally used for this purpose and while using suitable auxiliary substances, for example, solid or liquid carrier materials.

The dosage in which the compounds according to the invention may be used depend on the severity and the nature of the disease to be treated and on the way of administration. As a rule the dosage will be between 0.05 and 20 mg, preferably between 0.1 and 10 mg of active substance daily.

The compounds according to the invention can be prepared in a manner known for analogous compounds, for example:

a) by reaction of a compound of formula 6

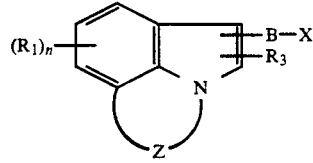
(6)

wherein $R_1$, $R_3$, n, Z and B have the meanings given in formula 2 and X is a group which may be replaced by a nucleophile, for example, a halogen atom, a 1-imidazolyl group, and alkoxy group, etc., with a compound of formula 7

Y—C—D (7)

wherein C and D have the meanings given in formula 2 and Y is a hydrogen atom or an alkali metal atom. The reaction is preferably carried out in a suitable solvent, for example, dichloromethane, pyridine, methanol, dimethylformamide, toluene, etc. In particular the compounds according to the invention can be prepared in a good yield i) by reaction, in the presence of active sodium alkanolate, of a compound of formula 6, wherein $R_1$, $R_3$, n, Z and B have the meanings mentioned in formula 2 and X is an alkoxy group, with a compound of formula 7 in which C and D have the meanings mentioned in formula 2 and wherein Y is a hydrogen atom. The reaction is preferably carried out in a suitable solvent, for example, toluene, xylene, etc., at temperatures between 20° and 160° C.; or ii) by reaction of a compound of formula 6, wherein $R_1$, $R_3$, n, Z and B have the meaning given in formula 2 and X is a halogen atom with a compound of formula 7, wherein Y is hydrogen, C represent a group N-$R_6$, and D and $R_6$ have the meaning given in formula 2. The reaction is preferably carried out in a suitable solvent, for example methylene chloride, acetonitrile, etc. at temperatures between 0° and 80° C.

The starting compounds of formula 6, to be used in these reactions i) and ii) wherein $R_1$, $R_3$, n, Z and B have the meanings mentioned in formula 2 and X is a hydroxy group or an alkoxy group, may be prepared in a manner known for analogous compounds and may be converted, likewise in known manner, into a compound of formula 6 wherein X is a group which may be replaced by nucleophiles, for example, a halogen atom, a 1-imidazolyl group, etc. Suitable methods of preparing this type of compounds are described in Heterocyclic Compounds (Houlinan, Part 1); J. Am. Chem. Soc. 60, 2414–16 (1938); J. C. S. Perkin Transactions (1981) 636–641. In particular, the starting compounds of formula 8

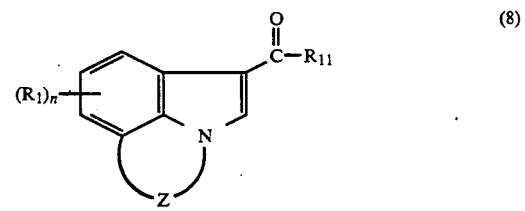
(8)

wherein $R_1$, n and Z have the meanings mentioned in formula 2 and $R_{11}$ is alkoxy, can be obtained by reaction of a compound of formula 9

(9)

with a compound of formula 10

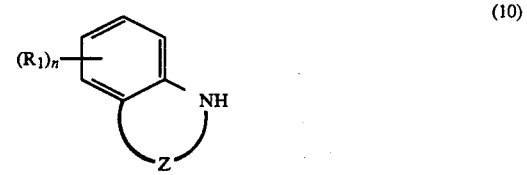
(10)

wherein $R_1$, n and Z have the meanings mentioned in formula 2. The reaction is preferably carried out in a suitable solvent, for example, tetrahydrofuran, ether, toluene, etc., at temperatures from 0°-100° C. The formed reaction product is then cyclised, preferably in the presence of a Lewis acid, for example, zinc chloride, aluminium chloride, etc. The cyclisation is preferably carried out in a suitable solvent, for example, alcohol, benzene, etc. at temperatures between 20° and 150° C.

The compounds of formulae 9 and 10 are known compounds or can be obtained analogously to known compounds.

Starting compounds of formula 11

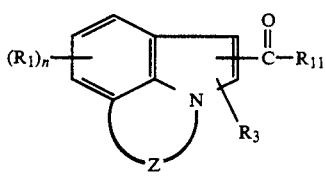

(11)

wherein $R_1$, n, Z and $R_3$ have the meanings given in formula 2, and $R_{11}$ is alkoxy, hydroxy or halogen in particular can be obtained by i) reaction of a compound of formula 12

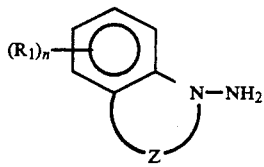

(12)

wherein $R_1$, n and Z have the above-mentioned meanings, with a compound of formula 13

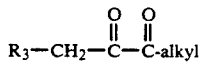

(13)

The reaction is preferably carried out in a solvent, for example alcohol, acetic acid, at temperatures between 20° and 120° C. The compounds of formula 11 so-obtained wherein $R_{11}$ is alkoxy can be converted in known manner into compounds wherein $R_{11}$ is hydroxy or halogen. The starting compounds having formula 12 and 13 are known compounds, or can be obtained analogous to known compounds; or ii) Vilsmeier-Haack formylation of a compound having formula 14

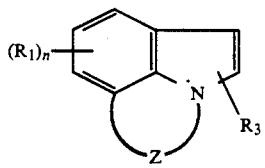

(14)

wherein $R_1$, n, $R_3$ and Z have the meanings given in formula 2, followed by oxidation of the formed aldehyde to the desired carboxylic acid, which may be converted in known manner to an analogous starting compound having formula 11. The starting compounds 14 are known or can be prepared analogous to known compound.

b) By substitution of the amine-hydrogen atom in group D in a compound of formula 2, wherein $R_1$, $R_3$, n, Z, B, C and D have the meanings mentioned in formula 2 with the proviso that the ring nitrogen atom in group D is secondary nitrogen atom, by a group $R_8$, wherein $R_8$ has the above-mentioned meaning, for example, by reacting of a compound of formula 2 with a suitable aldehyde or ketone under reducing conditions, or with a suitable halogen compound. The reaction is preferably carried out in a suitable solvent, for example, water, acetonitrile, alcohol, dimethylformamide, etc. at temperatures between 0° and 150° C.

The compounds having formula 2 wherein $R_1$, $R_2$, $R_3$, n and Z have the meanings mentioned in formula 2, on the understanding that $R_{10}$ is oxygen can be prepared in particular by oxidation of an analogous compound of formula 2 wherein $R_{10}$ is lacking, with a suitable oxidant, for example perbenzoic acid, peracetic acid, hydrogen, peroxide, etc., preferably in a suitable solvent, for example, chloroform, acetic acid or water, at temperatures between 0° and 100° C.

The invention will now be described in greater detail with reference to the ensuing specific examples.

EXAMPLE I (5,6-dihydro-4H-pyrrolo-[3,2,1-ij]-quinoline-1-yl)carboxylic acid (endo-8-methyl-8-azabicyclo-[3,2,1]-oct-3-yl) ester hydrochloride 0.7 g (30 mmol) of sodium were "dissolved" in 15 ml of methanol. 50 ml of toluene were added, after which the methanol was distilled off, while stirring, until the boiling-point of toluene had been reached. 3.45 g (15 mmol) of (5,6-dihydroxy-4H-pyrrolo-[3,2,1-ij]-quinolin-1-yl)-carboxylic acid ethyl ester and 4.2 g (30 mmol) of tropine were added to this suspension of sodium methanolate in toluene. This mixture was boiled for 4 hours while stirring. After cooling to room temperature, 100 ml of ether and 100 ml of water were added. The organic layer was separated, dried and evaporated to dryness. The residue (5.0 g) was purified by chromatography over 250 g of silica gel. Elution was carried out with a mixture of methanol and triethylamine (97:3). Yield 4.1 g (84%). The ester was converted, by means of alcoholic hydrochloric acid, into the hydrochloride, a substance having a melting-point (with gas formation) of 322° C.

The following compounds have been prepared in an analogous manner:

(1) (8-fluoro-5,6-dihydro-4H-pyrrolo-[3,2,1-ij]-quinolin-1-yl)-carboxylic acid-(endo-8-methyl-8-azabicyclo-[3,2,1]-oct-3-yl)ester hydrochloride;

(2) (5,6-dihydro-4H-pyrrolo-[3,2,1-ij]-quinolin-2-yl)-carboxylic acid-(endo-8-methyl-8-azabicyclo-[3,2,1]-oct-3-yl)ester hydrochloride; yield 58%, melting-point 295°-297° C. (decomposition).

(3) (2,3-dihydro-pyrrolo-[1,2,3-de][1,4]-benzothiazin-6-yl) carbocyclic acid (endo-8-methyl-8-azabicyclo-[3,2,1]-oct-3-yl)ester hydrochloride, the following structure of which was confirmed by $^{13}$C-NMR-analysis:

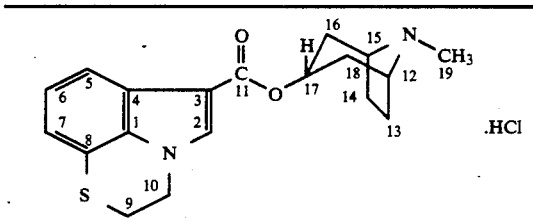

| 1 | 130.89 | S |
| --- | --- | --- |
| 2 | 132.76 | D |
| 3 | 107.89 | S |
| 4 | 125.58 | S |
| 5 | 118.23 | D # |
| 6 | 119.72 | D # |
| 7 | 122.74 | D # |
| 8 | 117.48 | S |
| 9 | 26.09 | T |
| 10 | 46.44 | T |
| 11 | 164.07 | S |
| 12 | 60.05 | D |
| 13 | 25.86 | T |

-continued

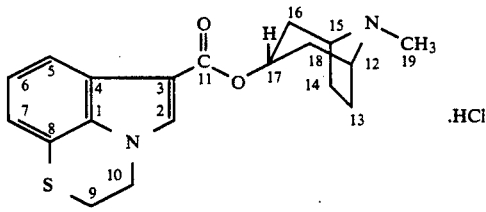

.HCl

| 14 | 25.86 | T |
| --- | --- | --- |
| 15 | 60.05 | D |
| 16 | 36.54 | T |
| 17 | 66.50 | D |
| 18 | 36.54 | T |
| 19 | 40.25 | Q |

(C-ATOM 2 IS SPLIT UP <1.7 HZ>)

EXAMPLE II

N-(endo-8-methyl-8-azabicyclo-[3,2,1]-oct-3-yl)-(5,6-dihydro-4H-pyrrolo-[3,2,1-ij]-quinolin-1-yl)-carboxamide hydrochloride 2.0 g (0.01 mol) of (5,6-dihydro-4H-pyrrolo-[3,2,1-ij]-quinolin-1-yl)-carboxylic acid were suspended in 50 ml of methylene chloride. 2.25 ml (0.03 mol) of thionyl chloride were added and the mixture was boiled for 1 hour, and evaporated in vacuo. The residue was dissolved in 50 ml of methylene chloride. 1.5 g (0.01 mol) of 3-amino-8-methyl-8-azabicyclo-[3,2,1]-octane were added, and the mixture was stirred for 30 minutes. Thereafter the reaction mixture was shaken with 2N sodium hydroxide, the methylene chloride layer was washed with water, dried and evaporated in vacuo. The residue was dissolved in ethyl acetate, and a mixture of 0.8 ml of acetyl chloride and 3 ml of alcohol was added. The solid substance was sucked off and dried. Yield 2.9 g (80%) of the desired hydrochloride having a melting-point of 280° C. (decomposition).

The following compounds have been prepared in an analogous manner:

(1) N-(endo-9-methyl-9-azabicyclo-[3,3,1]-non-3-yl)-(5,6-dihydro-4H-pyrrolo-[3,2,1-ij]-quinolin-1-yl)-carboxamide hydrochloride; yield 43%; melting-point 320°-323° C.

(2) N-(endo-8-methyl-8-azabicyclo-[3,2,1]-oct-3-yl)-N-methyl-(5,6-dihydro-4H-pyrrolo-[3,2,1-ij]-quinolin-1-yl)-carboxamide hydrochloride; yield 53%, melting-point 139°-141° C.

(3) N-(1-azabicyclo-[2,2,2]-oct-3-yl)-(5,6-dihydro-4H-pyrrolo-[3,2,1-ij]-quinolin-1-yl)-carboxamide hydrochloride; yield 31%. The product was obtained as a foam. The structure was confirmed by 13C-NMR analysis:

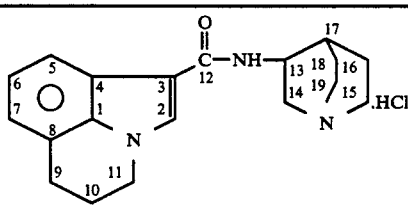

| 1 | 134.22 | S |
| --- | --- | --- |
| 2 | 129.33 | D |
| 3 | 110.22 | S |
| 4 | 124.42 | S |
| 5 | 118.69 | D |
| 6 | 119.33 | D |

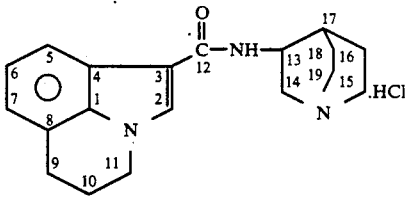

| 7 | 121.38 | D |
| --- | --- | --- |
| 8 | 122.06 | S |
| 9 | 24.63 | T |
| 10 | 22.69 | T |
| 11 | 44.39 | T |
| 12 | 165.42 | S |
| 13 | 45.87 | D |
| 14 | 53.91 | T |
| 15 | 46.96 | T |
| 16 | 24.33 | T |
| 17 | 25.68 | D |
| 18 | 19.43 | T |
| 19 | 46.46 | T |

(4) N-(1-azabicyclo-[2,2,2]-oct-3-yl)-(8-fluoro-5,6-dihydro-4H-pyrrolo-[3,2,1-ij]-quinolin-1-yl) carboxamide; yield 52%, melting-point 220°-221° C.;

(5) N-(1-azabicyclo-[2,2,2]-oct-3-yl)-(4,5,6,7-tetrahydroazepino-[3,2,1-jk]-indol-1-yl)-carboxamide; yield 43%, melting-point 66°-69° C.;

(6) N-(endo-8-methyl-8-azabicyclo-[3,2,1]-oct-3-yl)-(4,5,6,7-tetrahydroazepino-[3,2,1-jk]-indol-1-yl)-carboxamide;

(7) N-(1-azabicylco-[2,2,2]-oct-3-yl)-(6,7-dihydroindolo-[1,7-a,b]-[1]-benzazepin-1-yl)-carboxamide hydrochloride; yield 48%, melting-point 251°-252° C.;

(8) N-(1-azabicyclo-[2,2,2]-oct-3-yl)-(6,7-dihydroindolo-[1,7-ab]-[1]-benzazepin-2-yl)-carboxamide hydrochloride.

EXAMPLE III

N-(endo-8-(2-hydroxyethyl)-8-azabicylco-[3,2,1]-oct-3-yl)-(5,6-dihydro-4H-pyrrolo-[3,2,1-ij]-quinolin-1-yl)-carboxamide hydrochloride (a) 1.16 g (3,6 mmol) of N-(endo-8-methyl-8-azabicyclo-[3,2,1]-oct-3yl)-(5,6-dihydro-4H-pyrrolo-[3,2,1-ij]-carboxamide were dissolved in 50 ml of 1,2-dichloromethane and cooled to 0° C. under nitrogen. 0.51 g (3,6 mmol) of 1-chloroethyl-chloroformiate were added dropwise in 5 min. and the mixture was boiled for 1 hour and evaporated in vacuo. 50 ml of methanol were added to the residue, and the mixture was boiled for 30 min. The mixture was evaporated in vacuo and chromatographed over silicagel with methylene chloride/methanol/ammonia (84/15/1) as eluent. In this manner 0.7 g (63%) of the secundary amine was obtained.

(b) This product (2.3 mmol) was dissolved in 35 ml of acetonitrile. 0.18 ml (2.3 mmol) of 2-iodoethanol and 0.63 ml (4.6 mmol) of triethyl amine were added, and the mixture was boiled for 16 hours and then evaporated in vacuo. The residue was shaken with methylene chloride and 2N sodium hydroxide. The methylene chloride layer was dried and evaporated in vacuo. The residue was chromatographed over silicagel with methylene chloride/methanol/ammonia (84/15/1) as eluent. The desired fraction was evaporated in vacuo, and the residue was treated with 1.1 equivalent of alcoholic hydrochloric acid. The solid substance was sucked of and dried. In this manner 0.38 g (43%) of the above-mentioned hydrochloride was obtained, having a melting-point of 262°–263° C.

EXAMPLE IV

N-(1-azabicyclo-[2,2,2]-oct-3-yl-1-oxide)-(5,6-dihydro-4H-pyrrolo-[3,2,1-ij]-quinolin-1-yl)-carboxamide 0.31 g (1 mmol) of N-(1-azabicyclo-[2,2,2]-oct-3-yl)-5,6-dihydro-4H-pyrrolo-[3,2,1-ij]-quinolin-1-yl)-carboxamide were dissolved in 25 ml of chloroform. 0.172 g (1 mmol) of m-chloroperbenzoic acid were added, and the mixture was stirred for 24 hours at room temperature. The mixture was washed with methylene chloride and 2N sodium hydroxide, and evaporated in vacuo. The residue was chromatographed over silicagel. Yield 19%. $^{13}$C-NMR analysis:

| | |
|---|---|
| 1 | 133.74 |
| 2 | 129.09 |
| 3 | 109.04 |
| 4 | 124.33 |
| 5 | 118.51 |
| 6 | 119.04 |
| 7 | 121.05 |
| 8 | 122.22 |
| 9 | 24.76 |
| 10 | 22.26 |
| 11 | 43.85 |
| 12 | 164.54 |
| 13 | 46.38 |
| 14 | 65.43 |
| 15 | 60.06 |
| 16 | 23.39 |
| 17 | 23.77 |
| 18 | 20.38 |
| 19 | 59.53 |

Preparation of Intermediates a)
(5,6-dihydro-4H-pyrrolo-[3,2,1-ij]-quinolin-1-yl)-carboxylic acid ethyl ester 22.5 ml (approximately 0.15 mol) of 90% ethyl bromopyruvate were added dropwise and while stirring in approximately 0.5 hours at a temperature from 20°–35° C. to 37.5 ml (0.3 mol) of 1,2,3,4-tetrahydroquinoline in 100 ml of ether. Stirring was then continued for another hour. The separated 1,2,3,4-tetrahydroquinoline hydrobromide was sucked off. The filtrate was evaporated to dryness and the resulting residue (50 g of a viscous oil) was cyclised without purification.

150 ml of ethanol and 81 g of anhydrous zinc chloride were added to 50 g of the crude product. This mixture was boiled, while stirring, for 16 hours. A large part of the etahnol was then distilled off. After cooling to room temperature, 200 ml of 2N HCl and 500 ml of ether were added to the residue. This mixture was stirred until nearly everything had dissolved. The aqueous layer was extracted. The collected ether layers were dried and then evaporated to dryness. The residue (17 g) was purified by chromatography over 900 g of silicagel, elution being carried out with dichloromethane. Yield 8.8 g (26% with respect to 1,2,3,4-tetrahydroquinoline) having a melting-point of 70°–72° C.

b)
4,5,6,7-tetrahydro-pyrrolo-[3,2,1-jk]-1-benzapin-1-carboxylic acid 21.2 g (95 mmol) of 1-(α-chloroacetyl)-2,3,4,5-tetrahydro-1-benzazepine were heated (130° C.), 19,0 g (142 mmol) of aluminium chloride were added, and the mixture was kept at this temperature until gas development almost had ceased. Water and methylene chloride were then added and the mixture was shaken. The methylene chloride layer was separated, evaporated in vacuo, and chromatographed over silicagel with ether/petroleum ether (1/1) as eluent. Yield 8.85 g (50%) of 1,2,4,5,6,7-hexahydro-pyrrolo-[3,2,1-jk]-1-benzazepin-2-one.

7.5 g (0.04 mol) of this product were dissolved in 80 ml of diglyme, 5.7 g (0.044 mol) of borotrifluoro etherate were added, and the mixture was heated at 80° C. 1.7 g (0.044 mol) of sodium borohydride were added in small amounts, and the mixture was stirred at 80° C. for another 2 hours. 100 ml of 2N hydrochloric acid were added dropwise at 100° C., and the mixture was poured on ice, made alkaline, extracted with ether, washed with 6N hydrochloric acid, water and a sodium bicarbonate solution, and evaporated. Yield 3.3 g (48%) of 4,5,6,7-tetrahydro-pyrrolo-[3,2,1-jk]-1-benzazepine.

2.56 g (16,7 mmol) of phosphorus oxychloride were slowly added to 20 ml of dimethylformamide under nitrogen at 10°–20° C. This mixture was cooled to 10° C., and a solution of 2.6 g (15.2 mmol) of the obtained benzazepine in 20 ml of dimethylformamide was added dropwise. The mixture was stirred for 30 minutes at 10° C. and for 1 hour at 40° C. The mixture was poured on ice, made alkaline with 4 ml of 50% NaOH, boiled during 10 minutes and cooled. Then the mixture was extracted with ether, dried and evaporated. Yield 2.9 g (96%) of 1-formyl-4,5,6,7-tetrahydro-pyrrolo-[3,2,1-jk]-1-benzazepine.

1.0 g (5 mmol) of this product was dissolved in 75 ml of acetone, and a solution of 0.53 g (3.7 mmol) of potassium permanganate in 25 ml of water was added. The mixture was stirred for 1 hour, and filtered on hyflo. The filtrate was evaporated in vacuo, and 300 ml of ethyl acetate were added to the residue. The mixture was acidified with concentrated hydrochloric acid while stirring firmly, dried, filtered and evaporated. Yield 1.0 g (92%), melting-point 200°–201° C.

The following compounds have been prepared in a similar way:
(1) 5,6-dihydro-4H-pyrrolo-[3,2,1-ij]-quinolin-1-carboxylic acid; melting-point 221°–223° C.;
(2) 7-fluoro-5,6-dihydro-4H-pyrrolo-[3,2,1-ij]-quinolin-1-carboxylic acid; melting-point 231.5°–232° C.;
(3) 6,7-dihydro-indolo-[1,7-ab]-[1]-benzazepin-2-carboxylic acid.

c)
6,7-dihydro-indolo-[1,7-ab]-[1]-benzazepin-1-carboxylic acid 35 mmol (12.0 g, 60%) N-amino-iminodibenzyl and 4.5 g (38 mmol) of ethyl pyruvate were dissolved in 200 ml of alcohol and boiled for 30 minutes. Thereafter the reaction product of 15 ml of acetyl chloride and 50 ml of alcohol was added, and the mixture was boiled for 1 hour, evaporated and shaken with 2N sodium hydroxide and ethyl acetate. The ethyl acetate solution was evaporated and chromatographed over silicagel with ether/petroleum ether (1/9) as eluent. Yield 7.4 g (72%) oil.

The obtained product was boiled for 1 hour with an aqueous solution of KOH in alcohol, evaporated in vacuo; the residue was shaken with 2N hydrochloric acid and ethyl acetate. The ethyl acetate solution was washed with water, dried and evaporated. Yield 4.8 g (72%), melting-point 221°-222° C.

We claim:

1. An indole derivative of formula 2

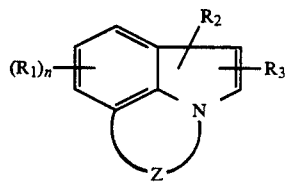

wherein $R_1$ is halogen;

n has a value of 0–2;

Z together with the carbon atom, the nitrogen atom and the intermediate carbon atom, forms a heterocyclic group consisting of 6 ring atoms in which, besides the nitrogen atom already present, a second hetero atom of S is present, which ring may be annelated with a benzene ring;

$R_3$ is hydrogen, halogen, alkyl, alkoxy or alkylthio having 1–4 carbon atoms; and $R_2$ is a group —CO—Y—$R_7$ wherein Y is an oxygen atom, or a group —$NR_6$, wherein $R_6$ is hydrogen or alkyl having 1–3 C-atoms, and $R_7$ represents a group of the formula

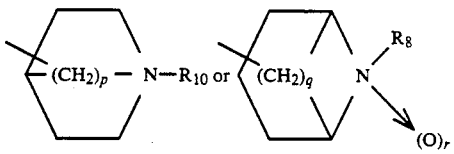

wherein p has the value 1 or 2, q has the value 2 or 3, $R_8$ is hydrogen or alkyl or hydroxyalkyl having 1 or 2 C-atoms, r is 0 or 1, and $R_{10}$ is absent or is an oxygen atom, or a pharmaceutically acceptable acid addition salt thereof.

2. A compound of formula (2,3-dihydro-pyrrolo-[1,2,3-de][1,4]-benzothiazin-6-yl)carbocyclic acid (endo-8-methyl-8-azabicyclo-[3,2,1]-oct-3-yl)ester hydrochloride, of the following structure:

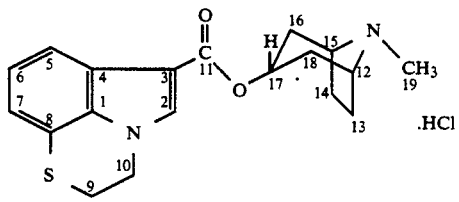

3. A pharmaceutical composition, which is a strong and selective antagonist of neuronal 5-hydroxytryptamine (5-HT) receptors, comprising an antagonistically effective amount of at least one compound as claimed in claim 1 as an active substance and an inert carrier.

4. A method of treating symptoms which are caused by over-excitation of 5-HT receptors, comprising using an effective amount of the composition as claimed in claim 3.

5. A pharmaceutical composition, which is a strong and selective antagonist of neuronal 5-hydroxytryptamine (5-HT) receptors, comprising an antagonistically effective amount of at least one compound as claimed in claim 2 as an active substance and an acceptable carrier.

6. A method of treating symptoms which are caused by over-excitation of 5-HT receptors, comprising using an effective amount of the composition as claimed in claim 5.

* * * * *